US008071569B2

(12) United States Patent
Mousa

(10) Patent No.: US 8,071,569 B2
(45) Date of Patent: Dec. 6, 2011

(54) OXIDIZED HEPARIN FRACTIONS AND THEIR USE IN INHIBITING ANGIOGENESIS

(76) Inventor: Shaker A. Mousa, Wynantskill, NY (US)

(*) Notice: Subject to any disclaimer, the term of this patent is extended or adjusted under 35 U.S.C. 154(b) by 0 days.

(21) Appl. No.: 13/029,584

(22) Filed: Feb. 17, 2011

(65) Prior Publication Data

US 2011/0200673 A1  Aug. 18, 2011

Related U.S. Application Data

(63) Continuation of application No. 10/667,216, filed on Sep. 19, 2003.

(60) Provisional application No. 60/411,851, filed on Sep. 20, 2002.

(51) Int. Cl.
*A61K 31/727* (2006.01)
*C08B 37/10* (2006.01)
*C07H 11/00* (2006.01)

(52) U.S. Cl. .................. 514/56; 536/124; 536/123.1

(58) Field of Classification Search .................. 514/56
See application file for complete search history.

(56) References Cited

U.S. PATENT DOCUMENTS

| | | | |
|---|---|---|---|
| 4,727,063 A | 2/1988 | Naggi et al. |
| 4,973,580 A | 11/1990 | Mascellani et al. |
| 5,092,885 A | 3/1992 | Yamada et al. |
| 5,112,946 A | 5/1992 | Maione |
| 5,192,744 A | 3/1993 | Bouck et al. |
| 5,202,352 A | 4/1993 | Okada et al. |
| 5,280,016 A | 1/1994 | Conrad et al. |
| 5,639,725 A | 6/1997 | O'Reilly et al. |
| 5,908,837 A | 6/1999 | Cohen et al. |
| 6,075,013 A | 6/2000 | Weitz et al. |
| 6,461,665 B1 | 10/2002 | Scholander |

OTHER PUBLICATIONS

Office Action (Mail Date Jun. 27, 2005) for U.S. Appl. No. 10/667,216,—filed Sep. 19, 2003, First Named Inventor: Shaker A. Mousa; Confirmation No. 7027.
Final Office Action (Mail Date Mar. 8, 2006) for U.S. Appl. No. 10/667,216,—filed Sep. 19, 2003, First Named Inventor: Shaker A. Mousa; Confirmation No. 7027.
Office Action (Mail Date Oct. 1, 2007) for U.S. Appl. No. 10/667,216,—filed Sep. 19, 2003, First Named Inventor: Shaker A. Mousa; Confirmation No. 7027.
Final Office Action (Mail Date Apr. 9, 2008) for U.S. Appl. No. 10/667,216,—filed Sep. 19, 2003, First Named Inventor: Shaker A. Mousa; Confirmation No. 7027.
Office Action (Mail Date Oct. 27, 2008) for U.S. Appl. No. 10/667,216,—filed Sep. 19, 2003, First Named Inventor: Shaker A. Mousa; Confirmation No. 7027.
Decision on Appeal (Mail Date Sep. 29, 2010) for U.S. Appl. No. 10/667,216,—filed Sep. 19, 2003, First Named Inventor: Shaker A. Mousa; Confirmation No. 7027.
Decision on Reconsideration—Denied (Mail Date Dec. 21, 2010) for U.S. Appl. No. 10/667,216,—filed Sep. 19, 2003, First Named Inventor: Shaker A. Mousa; Confirmation No. 7027.
Definition of inhibit, Dictionary.com, http://dictionary.reference.com, accessed online on Apr. 2, 2008. Final Office Action (Mail Date Apr. 9, 2008) for U.S. Appl. No. 10/667,216.
Kerbel et al. Cancer and Metastasis Reviews, 20, 2001, p. 79-86.*
Final Office Action (Mail Date Apr. 9, 2008) for U.S. Appl. No. 10/667,216.
Definition of Activated Partial Thromboplastin Time, Massacheusetts General Hospital Pathology Service, http://www.massgeneral.org, accessed on Oct. 20, 2008.* Office Action (Mail Date Oct. 27, 2008) for U.S. Appl. No. 10/667,216.
Definition of Heparin Antifactor Xa Assay, Massachusetts General Hospital Pathology Service, http://www.massgeneral.org, accessed online on Oct. 20, 2008.* Office Action (Mail Date Oct. 27, 2008) for U.S. Appl. No. 10/667,216.
Braswell, E., "Heparin: Molecular Weight and Degradation Studies," Biochim. Biophys. Acta 185: 103-116 (1968).
Kosakai et al., "Isolation and Characterization of Sulfated Disaccharides from the Deamination Products of Porcine Heparin (α-Heparin) and Whale Heparin (ω-Heparin), and a Comparison of the Deamination Products," J. Biochem. 83: 1567-1575 (1978).
Fransson et al., "Relationship Between Anticoagulant Activity of Heparin and Susceptibility to Periodate Oxidation," FEBS Letters 97: 119-123 (1979).
Fujita et al. "Improvement of Treadmill Capacity and Collateral Circulation as a Result of Exercise with Heparin Pretreatment in Patients with Effort Angina," Circulation 77: 1022-1029 (1988).
Rastinejad et al., "Regulation of the Activity of a New Inhibitor of Angiogenesis by a Cancer Suppressor Gene," Cell 56: 345-355 (1989).
Moses et al., "Identification of an Inhibitor of Neovascularization from Cartilage," Science 248: 1408-1410 (1990).
Blood et al., "Tumor Interactions with the Vasculature: Angiogenesis and Tumor Metastasis," Biochim. Biophys. Acta 1032: 89-118 (1990).
Oikawa et al., "Angiogenic Factor of a Rat Mammary Tumor Cell Line (RMT-1) (I). Secretion of Two Distinct Angiogenic Factors into Serum-Free Conditioned Medium by RMT-1 Cells," Cancer Letters 59: 57-66 (1991).
Buckley et al., "Enoxaparin: A Review of its Pharmacology and Clinical Applications in the Prevention and Treatment of Thromboembolic Disorders," Drugs 44: 465-497 (1992).
Clapp et al., "The 16-Kilodalton N-Terminal Fragment of Human Prolactin Is a Potent Inhibitor of Angiogenesis," Endocrinology 133: 1292-1299 (1993).
O'Reilly et al., "Angiostatin: A Novel Angiogenesis Inhibitor That Mediates the Suppression of Metastases," Cell 79: 315-328 (1994).
Chen et al., "A Strategy to Discover Circulating Angiogenesis Inhibitors Generated by Human Tumors," Cancer Research 55: 4230-4233 (1995).

(Continued)

*Primary Examiner* — Shaojia Anna Jiang
*Assistant Examiner* — Jonathan S Lau
(74) *Attorney, Agent, or Firm* — Schmeiser, Olsen & Watts, LLP

(57) ABSTRACT

The present invention relates to a heparin fraction comprising constituents having molecular weights of from about 2,000 to about 4,000 daltons, wherein from about 1% to about 100% of hydroxyl residues of the constituents are oxidized. The present invention also relates to methods of inhibiting angiogenesis and treating an angiogenesis-mediated disorder in a subject by administering a heparin fraction comprising constituents having molecular weights of from about 2,000 to about 30,000 daltons, wherein from about 1% to about 100% of hydroxyl residues of the constituents are oxidized. Another aspect of the present invention relates to compositions including the heparin fractions of the present invention.

19 Claims, 5 Drawing Sheets

OTHER PUBLICATIONS

Schnaper et al., "Plasminogen Activators Augment Endothelial Cell Organization In Vitro by Two Distinct Pathways," Journal of Cellular Physiology 165: 107-118 (1995).

Larnkjaer et al., "Isolation and Characterization of Hexasaccharides Derived from Heparin. Analysis of HPLC and Elucidation of Structure by 1H NMR," Carbohydrate Research 266: 37-52 (1995).

Strieter et al. "Interferon γ-Inducible Protein 10 (IP-10), a Member of the C-X-C Chemokine Family, is an Inhibitor of Angiogenesis," Biochemical and Biophysical Research Communications 210: 51-57 (1995).

Angiolillo et al., "Human Interferon-inducible Protein 10 is a Potent Inhibitor of Angiogenesis in Vivo," J. Experimental Medicine 182: 155-162 (1995).

Parangi et al., "Antiangiogenic Therapy of Transgenic Mice Impairs de novo Tumor Growth," Proc. Natl. Acad. Sci. USA 93: 2002-2007 (1996).

Risau, "Mechanisms of Angiogenesis," Nature 386: 671-674 (1997).

Mulloy et al., "Molecular Weight Measurements of Low Molecular Weight Heparins by Gel Permeation Chromatography," Thrombosis and Haemostasis 4: 668-674 (1997).

Dickinson et al., "Enoxaparin Increases the Incidence of Postoperative Intracranial Hemorrhage when Initiated Preoperatively for Deep Venous Thrombosis Prophylaxis in Patients with Brain Tumors," Neurosurgery 43: 1074-1081 (1998).

Linhardt et al., "Production and Chemical Processing of Low Molecular Weight Heparins," Seminars in Thrombosis and Haemostasis 25: 5-16 (1999).

Kosir et al., "Degradation of Basement Membrane by Prostate Tumor Heparanase," Journal of Surgical Research 81: 42-47 (1999).

Kakkar et al., "Antithrombotic Therapy in Cancer," BMJ 318: 1571-1572 (1999).

Hettiarachchi et al., "Do Heparins Do More than Just Treat Thrombosis? The Influence of Heparins on Cancer Spread," Thrombosis and Haemostasis 82: 947-952 (1999).

Mousa et al., "Comparative In Vitro Efficacy of Different Platelet Glycoprotein IIb/IIIa Antagonists on Platelet-Mediated Clot Strength Induced by Tissue Factor With Use of Thromboelastography," Arterioscler. Thromb. Vasc. Biol. 20: 1162-1167 (2000).

Arkel, "Thrombosis and Cancer," Seminars in Oncology 27: 362-374 (2000).

Zacharski et al., "Low-Molecular-Weight Heparin and Cancer," Seminars in Thrombosis and Hemostasis 26: 69-77 (2000).

Eriksson et al., "Fondaparinux Compared with Enoxaparin for the Prevention of Venous Thromboembolism After Hip-Fracture Surgery," N. Engl. J. Med. 345: 1298-1304 (2001).

Smorenburg et al., "The Complex Effects of Heparins on Cancer Progression and Metastasis in Experimental Studies," Pharmacological Reviews 53: 93-105 (2001).

Mousa et al., "Comparison of the Effect of Different Platelet GPIIb/IIa Antagonists on the Dynamics of Platelet/Fibrin-Mediated Clot Strength Induced Using Thromboelastography," Thrombosis Research 104: 49-56 (2001).

Morita et al., "High Affinity Binding of Heparin by Necrotic Tumour Cells Neutralises Anticoagulant Activity," Thromb. Haemost. 86: 616-622 (2001).

Prandoni, "Heparins and Venous Thromboembolism: Current Practice and Future Directions," Thromb. Haemost. 86: 488-498 (2001).

OXIDIZED HEPARIN FRACTIONS AND THEIR USE IN INHIBITING ANGIOGENESIS

This application is a continuation application claiming priority of Ser. No. 10/667,216, filed Sep. 19, 2003, which claims priority to the provisional application of Ser. No. 60/411,851, filed Sep. 20, 2002.

FIELD OF THE INVENTION

The present invention relates to oxidized heparin fractions and their use in inhibiting angiogenesis. The oxidized heparin fractions and compositions of the present invention can be used to treat angiogenesis-mediated disorders.

BACKGROUND OF THE INVENTION

Heparin is sulfate-containing polysaccharide which on a large scale is isolated from intestinal mucus from swine or lung from cattle. The average molecular weight for standard bovine heparin is more than 9,000 daltons and for standard porcine heparin more than 12,000 daltons. Traditionally, the clinical use of heparin has been associated with its anticoagulant and antithrombotic properties (Jorpes, *Heparin in Treatment of Thrombosis,* 2nd Ed. Oxford Medical Publications (1946)). Although the exact mechanism for heparin's antithrombotic properties is not known, it is believed to act by binding to antithrombin III. The heparin-antithrombin III complex inhibits the activity of numerous enzymes in the clotting cascade, including factors II (thrombin), IX/IXa, X/Xa, XI/XIa, and XIII (Carter et al., *Ann. Pharmacotherapy,* 27:1223-30 (1993); Buckley et al., *Drugs,* 44:465-97 (1992)). In addition, heparin induces release of other endogenous antithrombotic substances, such as tissue factor pathway inhibitor and tissue plasminogen activator. Heparin has also been found to accelerate coronary collateral development in dogs (Fujita et al., *Japanese Circulation Journal,* 51: 395-402 (1987)) and to improve collateral circulation in patients with effort angina (Fujita et al., *Circulation,* 77:1022-1029 (1988)). Other effects such as the "anti-complementary power of heparin" recognized by Ecker et al. in *J. Infect. Dis.* 44:250-253 (1929) and the finding by Clowes et al. in *Nature* 265:625-626 (1977) that heparin infusion following experimental injury suppressed the proliferation of smooth muscle cells, have not led to any widespread use of heparin for the treatment of diseases related to inflammation or to arteriosclerosis, which are associated with complement activation and smooth muscle cell proliferation respectively. The risk of hemorrhage is considered to be the main limitation for the clinical use of heparin in non-antithrombotic indications.

Angiogenesis is the development of new blood vessels from preexisting blood vessels (Mousa, In: *Angiogenesis Inhibitors and Stimulators: Potential Therapeutic Implications,* Landes Bioscience, Georgetown, Tex.; Chapter 1 (2000)). Physiologically, angiogenesis ensures proper development of mature organisms, prepares the womb for egg implantation, and plays a key role in wound healing. On the other hand, angiogenesis supports the pathological conditions associated with a number of disease states such as cancer, inflammation, and ocular diseases.

The development of vascular networks during embryogenesis or normal and pathological angiogenesis depends on growth factors and cellular interactions with the extracellular matrix (Breier et al., *Trends in Cell Biology* 6:454-456 (1996); Folkman, *Nature Medicine* 1:27-31 (1995); Risau, *Nature* 386:671-674 (1997)). Blood vessels arise during embryogenesis by two processes: vasculogenesis and angiogenesis (Blood et al., *Bioch. Biophys. Acta* 1032:89-118 (1990)). Vascular endothelial growth factor ("VEGF"), basic fibroblast growth factor ("bFGF" or "FGF2"), interleukin 8 ("IL-8") and tumor necrosis factor alpha ("TNF-α") are some of the growth factors that play a role in pathological angiogenesis associated with solid tumors, diabetic retinopathy, and rheumatoid arthritis (Folkman et al., *Science* 235:442-447 (1987)). Angiogenesis is generally absent in adult or mature tissues, although it does occur in wound healing and in embryogenesis (Moses et al., *Science* 248:1408-1410 (1990)).

Angiogenesis or "neovascularization" is a multi-step process controlled by the balance of pro- and anti-angiogenic factors. The latter stages of this process involve proliferation and the organization of endothelial cells (EC) into tube-like structures. Growth factors such as FGF2 and VEGF are thought to be key players in promoting endothelial cell growth and differentiation. The endothelial cell is the pivotal component of the angiogenic process and responds to many cytokines through its cell surface receptors and intracellular signaling mechanisms. Endothelial cells in culture are capable of forming tube-like structures that possess lumens. Therefore, endothelial cells are not only a prerequisite for neovascularization, but appear to be the basal structural requirement as well.

It has been proposed that inhibition of angiogenesis would be a useful therapy for restricting tumor growth Inhibition of angiogenesis can be achieved by inhibiting endothelial cell response to angiogenic stimuli as suggested by Folkman et al., *Cancer Biology* 3:89-96 (1992), where examples of endothelial cell response inhibitors such as angiostatic steroids, fungal derived products such fumagilin, platelet factor 4, thrombospondin, alpha-interferon, vitamin D analogs, and D-penicillamine are described. For additional proposed inhibitors of angiogenesis, see Blood et al., *Bioch. Biophys. Acta* 1032:89-118 (1990), Moses et al., *Science* 248:1408-1410 (1990), and U.S. Pat. Nos. 5,092,885, 5,112,946, 5,192, 744, and 5,202,352.

Native heparin or heparin fractions have also been proposed for use in the inhibition of angiogenesis. However, such use has not been widely accepted due to the high anticoagulant activity of such native heparin and heparin fractions. In particular, as described above, the risk of bleeding complications is considered to be the main limitation for the clinical use of heparin in non-antithrombotic indications.

The present invention is directed to overcoming these and other deficiencies in the art.

SUMMARY OF THE INVENTION

The present invention relates to a heparin fraction consisting of constituents having molecular weights of from about 2,000 to about 4,000 daltons, wherein from about 1% to about 100% of hydroxyl residues of the constituents are oxidized.

Another aspect of the present invention relates to a method of inhibiting angiogenesis. This method involves administering to a subject a heparin fraction comprising constituents having molecular weights of from about 2,000 to about 30,000 daltons, wherein from about 1% to about 100% of hydroxyl residues of the constituents are oxidized, whereby angiogenesis in the subject is inhibited.

Yet another aspect of the present invention relates to a method of treating an angiogenesis-mediated disorder in a subject. This method involves administering to a subject a heparin fraction comprising constituents having molecular weights of from about 2,000 to about 30,000 daltons, wherein from about 1% to about 100% of hydroxyl residues of the constituents are oxidized, whereby the angiogenesis-mediated disorder is treated.

The present invention also relates to a composition including from about 60% to about 100% of a heparin fraction consisting of constituents having molecular weights of from about 2,000 to about 4,000 daltons, wherein from about 1% to about 100% of hydroxyl residues of the constituents are oxidized, and from about 0% to about 40% of heparin, low molecular weight heparin, chondroitin sulfates, dermatan sulfates, heparan sulfates, heparin derivatives, or combinations thereof.

The present invention is based on the unexpected discovery that oxidized heparin fractions, in particular, those having low molecular weight ("LMWH") or ultra-low molecular weight ("ultra-LMWH"), with limited anticoagulant potency, enhance endothelial cell tissue factor pathway inhibitor ("TFPI") release and have potent anti-angiogenesis efficacy equal to or greater than standard anticoagulant heparin or LMWH. Preferred molecules are oxidized LMWH or ultra-LMWH fractions with high sulfation. The molecules can be used in pharmaceutical compositions to treat diseases which are angiogenesis-dependent. In addition, the heparin fractions of the present invention can be combined with other anti-angiogenesis agents, cytotoxic or chemotherapeutic agents, radiotherapy, tumor surgery, and other cancer-related therapies in cancer patients to prevent and treat tumor growth, tumor-induced angiogenesis, metastasis, tumor-mediated thrombosis, or other angiogenesis-mediated disorders.

DETAILED DESCRIPTION OF THE INVENTION

The present invention relates to a heparin fraction consisting of constituents having molecular weights of from about 2,000 to about 4,000 daltons, wherein from about 1% to about 100% of hydroxyl residues of the constituents are oxidized.

As used herein, low-molecular weight heparins (LMWHs) are heparin fractions having constituents having molecular weights of from about 2,000 to about 8,000 daltons. As used herein, ultra-LMWHs are heparin fractions having constituents having molecular weights of from about 2,000 to about 4,000 daltons. LMWHs are fractions (also referred to as fragments) of conventional porcine-derived or bovine-derived heparin or equivalent compounds which have been chemically generated. LMWHs were developed to provide more selective inhibition of enzyme function and reduce adverse effects. Heparin fractionation (or fragmentation) produces products which maintain activity against factor Xa and release antithrombotic factors, but have significantly less activity against factor IIa. In particular, the anticoagulant potency for native heparin fractions increases as the molecular weight distribution increases, with an optimal average molecular weight of 8,000-12,000 daltons. The ratio of anti-IIa/anti-Xa activity increases as the molecular weight distribution increases, with resulting increase in anticoagulant potency. Native heparin fractions, with molecular weight of 1,700-2,000 daltons are mainly anti-Xa, without significant anti-IIa. However, those fractions are still active anticoagulants and one of those fractions of 1,700 daltons (Pentasaccharide or Fondaparinux) is commercially available as an anticoagulant for the prevention of venous thromboembolic disorders (Turpie et al., *Arch Intern Med.* 162(16):1833-1840 (2002); Eriksson et al., *N. Engl. J. Med.* 345(18):1298-1304 (2001), which are hereby incorporated by reference in their entirety). Nevertheless, treatment with LMWHs provides antithrombotic effects with less anticoagulant effect, lessening the risk of hemorrhage.

Figure 1:
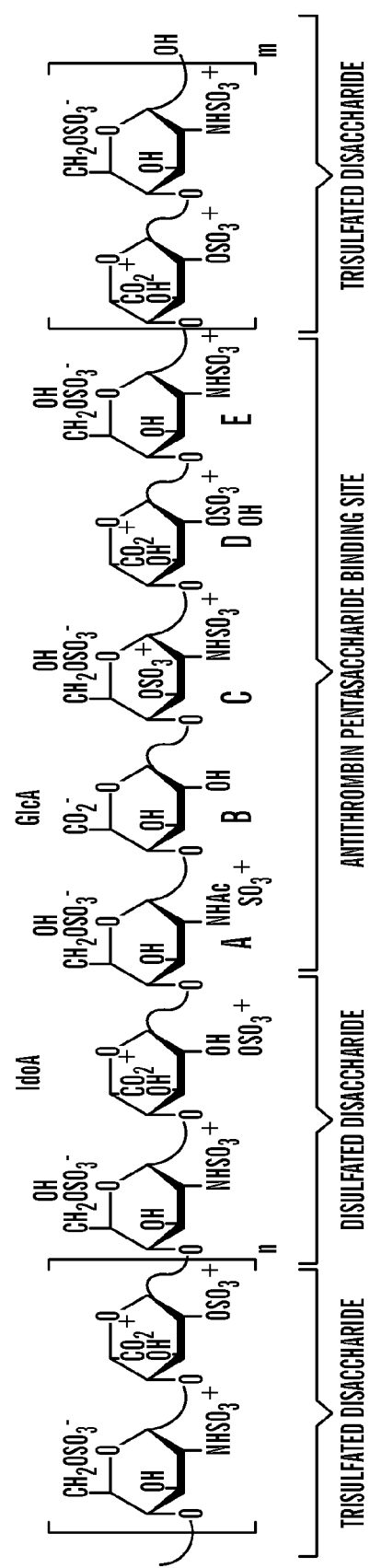
FIG. 1 is an illustration of the structure of a heparin constituent (n+m=16 for molecular weight of 12,000). Some structural variability both within and outside the antithrombin binding site is indicated by multiple substituents.

Standard or unfractionated heparin (UFH) is prepared by extraction from tissues typically obtained from either porcine intestine or bovine lung. However, UFH can be of any suitable origin, such as porcine, ovine, or bovine origin, and can be obtained from various tissues, including the mucus, lungs, or hides of the animals. Preferably, a heparin from porcine or ovine mucus or from bovine lung is used, and even more preferably from porcine mucus. Moreover, commercial pharmaceutical heparin is available. UFH is a complex polysaccharide composed of repeating disaccharides of uronic acid→glucosamine (see FIG. 1 for a sample structure of a heparin constituent). The disaccharide units may be biosynthetically modified, for example, as N-acetyl or N-sulfate glucosamine, 2-O-sulfate uronic acid and 6-O-sulfate and/or 3-O-sulfate glucosamine. The modifications are designed to change the activity of relevant groups of the molecules, thus to provide a wide range of heparin derivatives with greater ratio of anti-angiogenesis/anti-coagulant efficacy.

Heparin fractions (or fragments) can be obtained by fractionation of UFH using size exclusion chromatography for separation based on molecular weight distribution (Mulloy et al., *Thrombosis and Haemostasis,* 77(4):668-674 (1997); Linhardt et al., *Seminar in Thrombosis and Haemostasis,* 25(Suppl. 3):5-16 (1999), which are hereby incorporated by reference in their entirety). In particular, a double filtration procedure can be used, whereby a first filtration is used to obtain the upper limit of the molecular weight range (e.g., 4,000 or 8,000 daltons) and a second filtration is used to obtain the lower limit of the molecular weight range (e.g., 2,000 daltons).

In addition, heparin fractions (or fragments) can be produced as is generally known in the art by enzymatic or chemical cleavage. Examples of enzymatic or chemical cleavage methods include the following in which: (i) heparinase cleaves unfractionated heparin linkages between N-sulfated glucosamine and uronic acid with the formation of oligosaccharides bearing 4,5-unsaturated uronic acid at the non-reducing end; (ii) esters of the iduronic carboxyl groups of heparin are subjected to ββ-elimination at alkaline pH with the formation of 4,5-unsaturated uronic acid at the non-reducing end; (iii) non-sulfated uronic acid residues of heparins are cleaved by oxidation with either nitrous acid or periodate, followed by reduction of the resulting aldehyde(s) with borohydride and hydrolysis under mild acidic conditions, thus producing end groups with the remnant of the nonsulfated uronic acid; (iv) the glycosidic bonds of heparin are cleaved by a radical mechanism using hydrogen peroxide, known as oxidative-reductive depolymerization, resulting in fragments having reducing end groups; and (v) heparin chains are cleaved concomitant with sulfation by the action of a mixture of sulfuric and chlorosulfonic acids. Moreover, heparin fractions can be obtained by precipitation processes, such as fraction precipitation, which depend on the differential solubilities of fractions as a function of molecular weight in a given solvent system.

The obtained fractions can be optionally purified, for example by SAX (strong anion exchange) chromatography according to the methods known to those skilled in the art and in particular according to the methods described by Rice et al., *Carbohydrate Research,* 190:219-233 (1989) and Larnkjaer et al., *Carbohydrate Research,* 266:37-52 (1995), which are hereby incorporated by reference in their entirety.

Oxidation of heparin fractions in accordance with the present invention can be achieved using oxidizing agents, including, but not limited to, periodic acid, metals in high valence states, halogens, halogen atoms, and compounds with O—O bonds, such as $O_3$, diacyl peroxides, $H_2O_2$, and $O_2$. Such oxidizing agents and conditions for oxidation are known in the art and will not be described in detail herein. In one embodiment, oxidation is achieved using a periodate procedure, whereby fractions derived from UFH or super-sulfated heparin, as described below, are oxidized by periodic acid (Fransson, *Carbohydrate Res.,* 62:235-244 (1978); Conrad et al., *Heparin and Related Polysaccharides, Advances in Experimental Medicine and Biology* 313, Lane et al., eds., Plenum Publishing, New York, pp. 31-36 (1991), which are hereby incorporated by reference in their entirety). Alternatively, UFH or super-sulfated heparin can be oxidized prior to producing heparin fractions as described above. In yet another embodiment, UFH or super-sulfated heparin can be subjected to size exclusion chromatography both before and after oxidation. By oxidation of heparin fractions in accordance with the present invention, hydroxyl residues in the uronic acid and glucosamine monosaccharides are converted to aldehydes, which are then converted to acids. The percentage of hydroxyl residues that are oxidized in accordance with the present invention is determined by the length of incubation with the oxidizing agent and/or the quantity of oxidizing agent used. In one embodiment, from about 1% to about 100% of hydroxyl residues are oxidized. In one embodiment, from about 25% to about 100% of hydroxyl residues are oxidized. In another embodiment, from about 50% to about 100% of hydroxyl residues are oxidized. In yet another embodiment, from about 90% to about 100% of hydroxyl residues are oxidized.

Although not wishing to be bound by theory, it is believed that oxidation of LMWH ranging from about 2,000-8,000 daltons, particularly 2,000-4,000 daltons, results in weak anticoagulant activity while enhancing TFPI release from human endothelial cells and subsequently attaining potent anti-angiogenesis efficacy. With regard to anti-angiogenesis efficacy, native heparin fractions show increased anti-angiogenesis efficacy as a function of increased molecular weight, with a maximum potency at the 8,000-12,000 daltons. In contrast, oxidized small molecular weight heparin fractions between 2,000-4,000 daltons demonstrate potent anti-angiogenesis efficacy equivalent to that shown with the native fractions (8,000-12,000 daltons). This improved anti-angiogenesis potency is achieved without the increased anticoagulant potency seen with native heparin fractions. In contrast, the anticoagulant potency of oxidized low molecular weight heparin and ultra-low molecular weight heparin fractions is diminished. Thus, the small molecular weight heparin fractions have limited anticoagulant activity to avoid any bleeding complications upon dose escalation for the desired anti-angiogenesis efficacy. Such small molecular weight fractions also have preferred pharmacodynamic and pharmacokinetic properties that intervene in angiogenesis-mediated diseases.

In addition, the oxidized heparin fractions of the present invention reduce prolongation of prothrombin time (PT) or activated partial thromboplastin time (APTT) (see Example 6 (Table 2)) which allows the products of the invention to be administered at higher and more effective doses than standard heparin without the risk of bleeding. By reduced prolongation of PT or APTT is here meant a reduction of at least 75%.

In one embodiment of the present invention, the oxidized heparin fraction comprises constituents having a high sulfate to carboxylate ratio. As used herein, a high sulfate to carboxylate ratio ranges from about 2:1 to about 5:1. In a preferred embodiment, from about 50% to about 100% of primary hydroxyls in glucosamine residues and secondary hydroxyl groups in disaccharide units are substituted by O-sulfate esters. This high sulfate oxidized heparin fraction can be obtained using an enzymatic hydrolysis procedure as described in the Examples below (see also Mulloy et al., *Thrombosis and Haemostasis,* 77(4): 668-674 (1997); Linhardt et al., *Seminar in Thrombosis and Haemostasis,* 25(Suppl. 3):5-16 (1999), which are hereby incorporated by reference in their entirety). The oxidized heparin fraction can be chemically enriched with sulfate groups prior to or after oxidation. In another embodiment, the high sulfate oxidized heparin fraction is obtained by using as starting material a heparin which is rich in sulfate groups. High sulfate starting material can be obtained commercially (e.g., from Neoparin, Inc.). Additionally, methods known in the art, for example, obtaining heparin from bovine lung components can be used (Linhardt, et al., *Seminar in Thrombosis and Haemostasis,* 25(Suppl. 3):5-16 (1999), which is hereby incorporated by reference in its entirety), including employing a fractionation procedure that enriches the heparin with respect to highly sulfated components. Such a fractionation procedure may include: (1) precipitating the product from an aqueous solution of a sodium, calcium, zinc, or barium salt by a water miscible solvent and in the case of calcium, zinc, and barium salts, after the fractionation converting these salts to sodium salts; or (2) a chromatographic procedure involving hydrophobic interaction, cation exchange, or affinity chromatography.

Methods for chemical sulfation of the products of the invention should be mild enough not to cause depolymerization or degradation of the product being sulfated. For example, the products could be sulfated by treating their tributylammonium salts dissolved in dry dimethylformide at low temperature with a complex of sulfur trioxide and an organic base such as pyridine or triethylamine and then isolating and purifying the sulfated product using any one of the methods employed for fractionation in the periodate procedure. Since chemical sulfation of heparin as such generally decreases the anticoagulant activity of heparin as measured by the PT or APTT, a milder periodate procedure (for oxidation) may be used when combined with chemical sulfation compared to when the periodate procedure is used alone. In another embodiment of the invention, the preparation may begin with a mild partial chemical sulfation followed by a periodate procedure, which is a process preferred for native heparin low molecular weight fractions. Oxidized ultra LMWH fractions obtained from super-sulfated heparin show potent anti-angiogenesis activity, with minimal anticoagulant effect. Non-oxidized fractions obtained from super-sulfated heparin demonstrate a shift in the anti-angiogenesis/anticoagulant efficacy, but still retain significant anti-coagulant efficacy.

Another aspect of the present invention relates to a method of inhibiting angiogenesis. This method involves administering to a subject a heparin fraction comprising constituents having molecular weights of from about 2,000 to about 30,000 daltons, wherein from about 1% to about 100% of hydroxyl residues of the constituents are oxidized, whereby angiogenesis in the subject is inhibited.

As used herein, suitable subjects include, but are not limited to, mammals, including dogs, cats, rats, mice, and humans, and non-mammalian animals. In addition, suitable subjects include tissues obtained from or to be introduced into a subject, such as inflamed tissue, a solid tumor, retinal tissue, choridal tissue, and skin.

In one embodiment, from about 25% to about 100% of hydroxyl residues are oxidized. In another embodiment, particularly for ultra-LMWH fractions, from about 50% to about 100% of hydroxyl residues are oxidized. In yet another embodiment, from about 90% to about 100% of hydroxyl residues are oxidized.

In another embodiment, the fraction consists of constituents having molecular weights of from about 2,000 to about 8,000 daltons. In yet another embodiment, the fraction consists of constituents having molecular weights from about 2,000 to about 4,000 daltons.

Yet another aspect of the present invention relates to a method of treating an angiogenesis-mediated disorder in a subject. This method involves administering to the subject a heparin fraction comprising constituents having molecular weights of from about 2,000 to about 30,000 daltons, wherein from about 1% to about 100% of hydroxyl residues of the constituents are oxidized, whereby the angiogenesis-mediated disorder in the subject is treated.

In one embodiment, from about 25% to about 100% of hydroxyl residues are oxidized. In another embodiment, particularly for ultra-LMWH fractions, from about 50% to about 100% of hydroxyl residues are oxidized. In yet another embodiment, from about 90% to about 100% of hydroxyl residues are oxidized.

In another embodiment, the fraction consists of constituents having molecular weights of from about 2,000 to about 8,000 daltons. In yet another embodiment, the fraction consists of constituents having molecular weights from about 2,000 to about 4,000 daltons.

Suitable angiogenesis-mediated disorders in accordance with the present invention include, but are not limited to, tumors and cancer associated disorders (e.g., retinal tumor growth, benign tumors (e.g., hemangiomas, acoustic neuromas, neurofibromas, trachomas, and pyogenic granulomas), solid tumors, blood borne tumors (e.g., leukemias, angiofibromas, and kaposi sarcoma), tumor metastases, and other cancers which require neovascularization to support tumor growth), ocular neovascular-disorders (e.g., diabetic retinopathy, macular degeneration, retinopathy of prematurity, neovascular glaucoma, corneal graft rejection, and other ocular angiogenesis-mediated disorders), inflammatory disorders (e.g., immune and non-immune inflammation, rheumatoid arthritis, chronic articular rheumatism, inflammatory bowel diseases, psoriasis, and other chronic inflammatory disorders), endometriosis, other disorders associated with inappropriate or inopportune invasion of vessels (e.g., retrolental fibroplasia, rubeosis, and capillary proliferation in atherosclerotic plaques and osteoporosis), Osler-Webber Syndrome, myocardial angiogenesis, plaque neovascularization, telangiectasia, hemophiliac joints, and wound granulation. Other diseases in which angiogenesis plays a role in the maintenance or progression of the pathological state are known to those skilled in the art and are similarly intended to be included within the meaning of the term "angiogenesis-mediated" used herein.

In accordance with the methods of the present invention, the oxidized heparin fraction can be administered alone, or in combination with suitable pharmaceutical carriers or diluents. The diluent or carrier ingredients should be selected so that they do not diminish the therapeutic effects of the oxidized heparin fractions or compositions. Suitable pharmaceutical compositions include those which include a pharmaceutical carrier and, for example, one or more of an oxidized heparin fraction as described herein. A pharmaceutically acceptable medium can additionally contain physiologically acceptable compounds that act, for example, to stabilize or increase the absorption of the oxidized heparin fraction, analogue, mimetic, or chemical derivative. Such physiologically acceptable compounds include, for example, carbohydrates such as glucose, sucrose, or dextrans; antioxidants such as ascorbic acid or glutathione; chelating agents such as EDTA, which disrupts microbial membranes; divalent metal ions such as calcium or magnesium; low molecular weight proteins; lipids or liposomes; or other stabilizers or excipients.

The oxidized heparin fractions and compositions herein can be made up in any suitable form appropriate for the desired use; e.g., oral, parenteral, or topical administration. Examples of parenteral administration are intraventricular, intracerebral, intranasal, intraocular, intramuscular, intravenous, intraarterial, intraperitoneal, by intraversal instillation, intralesion, rectal, and subcutaneous administration. Administration can also be achieved by application to mucous membranes. The preferred route for administration is intravenous or subcutaneous. In cases where the oxidized heparin fractions or compositions are administered topically or parenterally, it is preferred that they be pre-hydrolyzed.

Suitable dosage forms for oral use include tablets, dispersible powders, granules, capsules, suspensions, syrups, and elixirs. Inert diluents and carriers for tablets include, for example, calcium carbonate, sodium carbonate, lactose, and talc. Tablets may also contain granulating and disintegrating agents, such as starch and alginic acid; binding agents, such as starch, gelatin, and acacia; and lubricating agents, such as magnesium stearate, stearic acid, and talc. Tablets may be uncoated or may be coated by known techniques to delay disintegration and absorption. Inert diluents and carriers which may be used in capsules include, for example, calcium carbonate, calcium phosphate, and kaolin. Suspensions, syrups, and elixirs may contain conventional excipients, such as methyl cellulose, tragacanth, sodium alginate; wetting agents, such as lecithin and polyoxyethylene stearate; and preservatives, such as ethyl-p-hydroxybenzoate.

Dosage forms suitable for parenteral administration include solutions, aqueous and non-aqueous suspensions which can include suspending agents and thickening agents, dispersions, emulsions, and the like. They may also be manufactured in the form of sterile solid compositions which can be dissolved or suspended in sterile injectable medium immediately before use. They may contain suspending or dispersing agents known in the art. The solutions, suspensions, dispersions, emulsions, and the like can additionally contain, for example, anti-oxidants, buffers, bacteriostats, and solutes which render the formulation isotonic with the blood of the intended recipient. The formulations can be presented in unit-dose or multi-dose containers, for example, sealed ampoules and vials. Extemporaneous injection solutions and suspensions can be prepared from sterile powders, granules, and tablets of the kind previously described.

For oral administration either solid or fluid unit dosage forms can be prepared. For preparing solid compositions, such as tablets, a suitable oxidized heparin fraction or composition, as disclosed above, is mixed with conventional ingredients, such as talc, magnesium stearate, dicalcium phosphate, magnesium aluminum silicate, calcium sulfate, starch, lactose, acacia methylcellulose, and functionally similar materials as pharmaceutical diluents or carriers. Capsules are prepared by mixing the disclosed oxidized heparin fractions or compositions with an inert pharmaceutical diluent and filling the fixture into a hard gelatin capsule of appropriate size. Soft gelatin capsules are prepared by machine encapsulation of a slurry of the oxidized heparin fraction or composition with an acceptable vegetable oil, light liquid petrolatum, or other inert oil.

Fluid unit dosage forms for oral administration such as syrups, elixirs, and suspensions can be prepared. The water-soluble forms can be dissolved in an aqueous vehicle together with sugar, aromatic flavoring agents, and preservatives to form a syrup. An elixir is prepared by using a hydro-alcoholic (ethanol) vehicle with suitable sweeteners, such as sugar and saccharin, together with an aromatic flavoring agent. Suspensions can be prepared with a syrup vehicle with the aid of a suspending agent, such as acacia, tragacanth, methylcellulose, and the like.

When the oxidized heparin fractions or compositions are administered orally, suitable daily dosages can be based on suitable doses of heparin. Typically, for oral administration, suitable daily doses are from about 10 mg to about 1,000 mg of the oxidized heparin fraction or composition per kilogram of the subject's body weight. Alternatively, the oxidized heparin fractions or compositions can be administered orally in foodstuffs and with excipients known in the art that enhance oral bioavailability.

For parenteral administration, fluid unit dosage forms are prepared utilizing the aforementioned oxidized heparin fractions or compositions and a sterile vehicle, water being preferred. The oxidized heparin fraction or composition, depending on the vehicle and concentration used, can be either suspended or dissolved in the vehicle. In preparing solutions, the oxidized heparin fraction or composition can be dissolved in water for injection and filter sterilized before filling into a suitable vial or ampule and sealing. Advantageously, adjuvants, such as a local anesthetic, preservative, and buffering agents, can be dissolved in the vehicle. To enhance the stability, the fluid unit dosage form can be frozen after filling into the vial, and the water removed under vacuum. The dry lyophilized powder is then sealed in the vial, and an accompanying vial of water for injection is supplied to reconstitute the liquid prior to use. Parenteral suspensions are prepared in substantially the same manner except that the oxidized heparin fraction or composition is suspended in the vehicle instead of being dissolved, and sterilization cannot be accomplished by filtration. The oxidized heparin fraction or composition can be sterilized by exposure to ethylene oxide before suspending in the sterile vehicle. Advantageously, a surfactant or wetting agent is included in the parenteral suspension to facilitate uniform distribution of the oxidized heparin fraction or composition. Parenteral dosages typically can range from about 1 mg to about 100 mg of oxidized heparin fraction or composition per kilogram of the subject's body weight per day.

Alternatively, the oxidized heparin fraction or composition can be used in polymeric formulations and sustained release formulations and surgically implanted using conventional methods. Suitable sustained release matrices include those made of ethylene vinyl acetate and other biocompatible polymers. The oxidized heparin fraction can be covalently attached by surface grafting or co-polymerization, non-covalently incorporated into a matrix, or otherwise encapsulated as biomedical materials. Modulation and control of new blood vessel formation is an essential part of formation of tissue engineering materials where a balance of pro-angiogenic and anti-angiogenic factors must be maintained. The oxidized heparin fraction may be used in conjunction with known promoters of angiogenesis or functional biomedical materials, such as implant and prosthetic materials, scaffolds for tissue engineering, wound healing materials, or ex vivo artificial organ materials, that modulate new blood vessel formation in tissue. This is one example of a drug delivery method involving conjugation of the anti-angiogenesis heparin fraction to a carrier material that can be used to locally deliver the anti-angiogenic effects of such a formulation in angiogenesis-dependent disorders.

For topical administration, carriers, such as phospholipid vesicles, which contain the aforementioned oxidized heparin fraction or composition may facilitate uptake through the skin.

In one embodiment, the oxidized heparin fraction or composition is used in conjunction with other angiogenesis inhibitors. Angiogenic inhibitors are known in the art and can be prepared by known methods. For example, angiogenic inhibitors include integrin inhibitory compounds such as $\alpha v$ integrin inhibitory antibodies, cell adhesion proteins, or functional fragments thereof which contain a cell adhesion binding sequence. Additional angiogenic inhibitors include, for example, angiostatin (see, e.g., U.S. Pat. No. 5,639,725, which is hereby incorporated by reference in its entirety), functional fragments of angiostatin, endostatin (see, e.g., PCT publication WO 97/15666, which is hereby incorporated by reference in its entirety), fibroblast growth factor (FGF) inhibitors, FGF receptor inhibitors, VEGF inhibitors (VEGF antibodies, VEGF trap, VEGF receptor blockers, and other mechanisms of VEGF inhibition), thrombospondin, platelet factor 4, interferon, interleukin 12, thalidomide, and compounds involved in other mechanisms for the inhibition of angiogenesis. For a description of angiogenic inhibitors and targets set forth above, see, for example, Chen et al., *Cancer Res.* 55:4230-4233 (1995), Good et al., *Proc. Natl. Acad. Sci. USA* 87:6629-6628 (1990), O'Reilly et al., *Cell* 79:315-328 (1994), Parangi et al., *Proc. Natl. Acad. Sci. USA* 93:2002-2007 (1996), Rastinej ad et al., *Cell* 56:345-355 (1989), Gupta et al., *Proc. Natl. Acad. Sci. USA* 92:7799-7803 (1995), Maione et al., *Science* 247:77-79 (1990), Angiolillo et al., *J. Exp. Med.* 182:155-162 (1995), Strieter et al., *Biochem. Biophys. Res. Comm.* 210:51-57 (1995); Voest et al., *J. Natl. Cancer Inst.* 87:581-586 (1995), Cao et al., *J. Exp. Med.* 182:2069-2077 (1995), and Clapp et al., *Endocrinology* 133: 1292-1299 (1993), which are hereby incorporated by reference in their entirety. For a description of additional angiogenic inhibitors see, for example, Blood et al., *Bioch. Biophys Acta.,* 1032:89-118 (1990), Moses et al., *Science,* 248:1408-1410 (1990), Ingber et al., *Lat Invest.,* 59:44-51 (1988), and U.S. Pat. Nos. 5,092,885 and 5,112,946, which are hereby incorporated by reference in their entirety.

In another embodiment, the oxidized heparin fraction or composition is used in conjunction with native heparin or non-oxidized heparin fractions. In particular, the present invention relates to a composition including, as an active ingredient, 60-100% oxidized heparin fraction, preferably LMWH, and most preferably ultra-LMWH, in accordance with the present invention, and 0-40% native heparin or LMWH. Additionally, the oxidized heparin fraction could be combined with various standard non-heparin anticoagulants such as direct anti-Xa, direct anti-IIa (anti-thrombin), anti-tissue factor, or anti-VIIa compounds, as described above with regard to native heparin or heparin fractions (see, e.g., Spencer et al., *Curr. Cardiol. Rep.* 2(5):395-404 (2000); Gustafsson, *J. Intern. Med.* 254(4):322-334 (2003); Vlasuk et al., *Trends Cardiovasc. Med.* 12(8):325-331 (2002); Wong et al., *Cardiovasc. Drug Rev.* 20(2):137-152 (2002); Uchiba et al., *Thromb. Res.* 74(2):155-161 (1994); Presta et al., *Thromb. Haemost.* 85(3):379-389 (2001); Parlow et al., *J. Med. Chem.* 46(19):4050-4062 (2003); Parlow et al., *J. Med. Chem.* 46(19):4043-4049 (2003), which are hereby incorporated by reference in their entirety). Such compositions enable various degrees of anticoagulant effect to be achieved to inhibit, for example, tumor-associated thrombosis in cancer patients.

A small percentage of patients who are administered heparin over an extended period of time develop heparin-induced thrombocytopenia (HIT). For this reason, it may be advantageous, at least for certain patients, to administer heparin-like substances instead of heparin in conjunction with the disclosed oxidized heparin fractions. Suitable heparin-like substances include, but are not limited to chondroitin sulfates, dermatan sulfates, heparan sulfates, and heparin derivatives.

Chondroitin sulfates are structurally complex, sulfated, linear polysaccharides known as galactosaminoglycans (GAGS) comprising alternating uronic acid and N-acetyl-D-galactosamine residues. Chondroitin sulfates are localized on cell surfaces and in the extracellular matrix, and are important in cell to cell communications. They are the predominant GAGS comprising the proteoglycans produced by monocyte/macrophages. Chondroitin Sulfate A (CSA) includes unsulfated glucuronic acid 1→3 linked to 4-O-sulfated N-acetyl-D-galactosamine which in turn is attached to the next glucuronic acid by a 1→4 linkage. Chondroitin Sulfate B, also known as Dermatan Sulfate or beta-heparin, is similar to CSA except that it contains iduronic acid instead of glucuronic acid. Chondroitin Sulfate C(CSC) has a 6-O-sulfate group and Chondroitin Sulfate E has a 4,6-di-O-sulfate on N-acetyl-D-galactosamine, in place of a 4-O-sulfate found in CSA. Suitable chondroitin sulfates include those described in Bjornsson et al., *Thromb. Res.*, 27:15-21 (1982); U.S. Pat. No. 3,895,106 to Morrison; Mazieres et al., *Rev. Rhum. Mal. Osteoartic.*, 59:466-72 (1992); Nadkarni et al., *Carbohydrate Res.*, 290:87-96 (1996), which are hereby incorporated by reference in their entirety.

Dermatan sulfate, also known as ββ-heparin or chondroitin sulfate B is a polysaccharide composed of repeating uronic acid→N-acetyl-D-galactosamine disaccharides joined by 1, 3 and 1, 4 linkages. It is initially formed as a polymer composed of repeating glucuronosyl→galactosyl→galactosyl→xylosyl linkage regions. In its biosynthesis, some of the D-glucuronic acid residues are epimerized at C-5, converting them to L-iduronic acid residues, which is then followed by O-sulfation primarily at C-4, but also at C-6. Dermatan sulfate functions as an anticoagulant by catalyzing the inhibition of thrombin as it is formed in plasma. It specifically activates heparin cofactor II (HCII), a plasma protease inhibitor which inhibits thrombin but not other proteases involved in haemostasis. HCII is activated by fractions of 12 or more residues in length that contain an octasaccharide sequence required for binding to the inhibitor. Suitable dermatan sulfates include those disclosed in Tollefsen, *Heparin and Related Polysaccharides*, Lane et al., eds., Plenum Press, New York, pp. 167-76 (1992), Van Gorp, *Clin. Haemost. Rev.*, 9:17-8 (1995); Nadkarni et al., *Carbohydrate Res.*, 290:87-96 (1996), which are hereby incorporated by reference in their entirety.

Heparan sulfate, otherwise known as heparin monosulfate, is a generic term describing polysaccharides which are linear. The heterogeneity in chemical composition and negative charge density of heparan sulfate contribute to diverse pharmacological actions. Suitable heparan sulfates are disclosed, for example, in Griffin et al., *Carbohydrate Res.*, 276:183-197 (1995), which is hereby incorporated by reference in its entirety.

Heparin derivatives can be obtained by deaminative hydrolysis of unfractionated heparin with nitrous acid to selectively cleave the glycosidic bonds of the N-sulfated glucosamine residues with formation of di-, tetra-, hexa-, and higher saccharides terminated with 2,5-anhydro-D-mannose (AM) residues as reducing terminal groups. The terminal AM residues may be stabilized with sodium borohydride or coupled to an aminated surface by reductive amination. Periodate causes the cleavage of carbon-carbon bonds if both adjacent carbons bear hydroxyl groups, or a hydroxyl group and an amino group. Unsulfated uronic acid residues in heparin are susceptible to periodate oxidation or Smith degradation. Fragments from periodate-oxidized heparin are larger than those obtained by nitrous acid degradation, reflecting relatively low contents of nonsulfated uronic acids. Those heparins containing aldehyde (CHO) moieties undergo reversible Schiff-base reactions with organic amines, and when treated with sodium cyanoborohydride, the Schiff base intermediate can be reduced to its corresponding amine forming an irreversible bond. In both these instances, the ATIII-binding site remains functionally intact. Suitable heparin derivatives are described, for example, in Kosakai et al., *J. Biochem.*, 83:1567-75 (1978); Braswell, *Biochim. Biophys. Acta*, 158:103-106 (1968); Fransson et al., *FEBS Lett.*, 97:119-23 (1979); Nagasawa et al., *Meth. Carbohydrate Chem.*, VIII: 291-4 (1980); Liu et al., *J. Pharm. Sci.*, 83:1034-1039 (1984), which are hereby incorporated by reference in their entirety.

Mixtures of heparin-like substances can also be used. One example of such a mixture is Danaparoid™ sodium. Danaparoid™ sodium is an alternative anticoagulant in patients who develop heparin-induced thrombocytopenia (HIT) from heparin therapy. Danaparoid™ is a low molecular weight heparinoid derived from porcine gut mucosa. Its active components consist of heparan sulfate, dermatan sulfate, and chondroitin sulfate. The major difference between Danaparoid™ and other low molecular weight heparins (LMWHs) is that Danaparoid™ is devoid of heparin or heparin fragments. However, similar to LMWHs, it exerts its antithrombotic effect principally through anti-thrombin III-mediated inhibition of factor Xa and, to a much lesser extent, thrombin.

In yet another embodiment, the modified LMWH is used in conjunction with other therapies, such as standard anti-inflammatory therapies, standard ocular therapies, standard dermal therapies, radiotherapy, tumor surgery, and cytotoxic agents or conventional chemotherapy directed against solid tumors and for the control of establishment of metastasis. The administration of the angiogenesis inhibitor is typically conducted during or after chemotherapy at time where the tumor tissue should respond to toxic assault by inducing angiogenesis to recover by the provision of a blood supply and nutrients to the tumor tissue. Additionally, it is preferred to administer such angiogenesis inhibitors after surgery where solid tumors have been removed as a prophylaxis against metastasis. Suitable cytotoxic or chemotherapeutic agents are known in the art and include, but are not limited to, nitrogen mustard, aziridine thiotepa, alkyl sulfonate, nitrosoureas, platinum complexes, non-classic alkylators, folate analogs, purine analogs, adenosine analogs, pyrimidine analogs, substituted urea, antitumor antibiotics, microtubule agents, and asparaginase.

The present invention also relates to a composition including from about 60% to about 100% of a heparin fraction consisting of constituents having molecular weights of from about 2,000 to about 4,000 daltons, wherein from about 1% to about 100% of hydroxyl residues of the constituents are oxidized, and from about 0% to about 40% of heparin, low molecular weight heparin, chondroitin sulfates, dermatan sulfates, heparan sulfates, heparin derivatives, or combinations thereof (i.e., a non-oxidized heparin, LMWH, or equivalent). In a preferred embodiment, the composition includes at least 1%, more preferably, at least 5% of the heparin, low molecular weight heparin, chondroitin sulfates, dermatan sulfates, heparan sulfates, heparin derivatives, or combinations thereof.

The present invention is further illustrated by the following examples.

EXAMPLES

Example 1

Materials

All reagents were chemical grade and purchased from Sigma Chemical Co. (St. Louis, Mo.) or through VWR Scientific (Bridgeport, N.J.). Cortisone acetate, bovine serum albumin (BSA), and gelatin solution (2% type B from bovine skin) were purchased from Sigma Chemical Co. (St. Louis, Mo.). M199 growth medium with Earl's salts, basic FGF, Insulin-Transferrin-Selenium-G Supplement (I-T-Se) 100×, Dulbecco's phosphate buffered salt solution (PBS) with and without $Ca^{+2}$ and $Mg^{+2}$, and 0.5 M EDTA were obtained from Gibco BRL (Grand Island, N.Y.). Human umbilical vein endothelial cells (HUVEC), endothelial cell basal medium (serum-free, EBM), endothelial growth medium (EGM) (supplemented with growth factors, fetal calf serum), and 0.025% trypsin/0.01% EDTA solution were purchased from Clonetics Inc. (San Diego, Calif.). Human prostrate (TSU-Pr) tumor cells were obtained from American Type Culture Collection (Rockville, Md.). Matrigel® matrix and human collagen type III were purchased from Becton Dickinson (Bedford, Mass.). HEMA-3 fixative and staining solutions were purchased from Biochemical Sciences, Inc. (Swedesboro, N.J.). Fertilized chicken eggs were purchased from Charles River Laboratories, SPAFAS Avian Products & Services (North Franklin, Conn.).

Example 2

Formation of Oxidized Ultra-LMWH

Standard bovine lung or porcine heparin (10 g), average molecular weight of 10,000 or 12,000 daltons, respectively, were used as the starting materials and were obtained from Sigma (Saint Louis, Mo.) and Neoparin, Inc. (San Lenadro, Calif.). The porcine heparin was fractionated by subjecting it to gel permeation chromatography on a Sephadex G-75 column, in which 10.00 g of porcine heparin was dissolved in 0.2 M sodium chloride and was then passed through the column at a rate of 1.0 ml/min A molecular weight fraction with average molecular weights ranging from 2,000-4,000 daltons was collected and desalted by ultrafiltration. Freeze-drying afforded 1.5 g of ultra-LMWH. Sodium periodate (0.3 g) dissolved in the sodium acetate buffer (40 ml) was added and the mixture was stirred for 2 days. Ethylene glycol (2 ml) was added to destroy excess periodate and the mixture was left at room temperature for a few hours. The solution was desalted on a Sephadex G-15 column. The fraction containing the desalted product was freeze dried resulting in 1.0 g of periodate oxidized heparin.

The periodate oxidized ultra-LMWH was dissolved in 0.02 M sodium hydroxide (0.1 liter) and was left at room temperature for 40 minutes and then reduced by sodium borohydride (0.1 g) for 2.5 hours. Excess sodium borohydride was decomposed by acetic acid (1 ml). This solution was then fractionated by ion exchange chromatography on a DEAE-Sepharose column A fraction was eluted, collected, and desalted using a hollow fiber (Amicon H1P3-20, cutoff 3,000 daltons). The heparin derivative was precipitated by the addition of cold ethanol (2.5 times the weight of the retentate). The precipitate was collected and dried in vacuum yielding 0.75 g of ultra-LMWH derivative 1.

Bovine lung heparin (2.0 g) was dissolved in sodium acetate buffer (50 ml) (0.05 M sodium acetate, 0.2 M sodium chloride, pH 4.0) and cooled to 4° C. Sodium periodate (0.2 g) dissolved in the sodium acetate buffer (50 ml) was added and the solution was left at 7° C. for three days. Ethylene glycol (2 ml) was added to destroy excess periodate and the solution was left at room temperature for an hour, and then desalted by ultrafiltration (Amicon YM2). The retentate was neutralized to pH 6.5 and freeze-dried yielding 1.78 g periodate oxidized heparin. The periodate oxidized heparin (1.60 g) was dissolved in 0.1 M sodium hydroxide (80 ml) and was left at room temperature for two hours and then reduced by sodium borohydride (80 mg) for three hours. Excess sodium borohydride was decomposed by acetic acid (2 ml), neutralized to pH 6.5, and fractionated by ultrafiltration using a membrane with a cutoff of 4,000 daltons. The ultra-LMWH molecular weight fraction retained on the filter was freeze dried (ultra-LMWH derivative 2).

Example 3

Formation of Oxidized Super-Sulfated Ultra-LMWH

Porcine mucosa heparin (10.0 g) was dissolved in water (75 ml) and passed through a cation exchange resin (Dowex 50WX8 in hydrogen form) (2.5×24 cm) and eluted with water (150 ml). The eluate was neutralized with tri-n-butylamine-ethanol (1:9) (50 ml) to pH 5.5 and extracted with diethyl ether (2×150 ml). The aqueous phase was freeze-dried to yield 7.5 g of product. The tributylammonium salt (0.50 g) was dried in vacuum and dissolved in dry N,N-dimethylformamide (5 ml) and sulfur trioxide triethylamine complex (0.15 g) was added. The solution was kept at room temperature for 18 hours and then poured into 3% sodium acetate in ethanol (45 ml). The mixture was centrifuged and the precipitate washed with ethanol (2×30 ml), dissolved in 2 M sodium chloride, and ultra-filtrated (Amicon YM1, cutoff 1000). The retentate was washed with water and freeze-dried.

The sulfated heparin (2.0 g) was dissolved in sodium acetate buffer (50 ml) (0.05 M sodium acetate, 0.2 M sodium chloride, pH 5.0). This solution was fractionated by ion exchange chromatography on a DEAE-Sepharose column. A fraction which eluted was collected and further fractionated by ultrafiltration using a membrane with a cutoff of 4,000 daltons (Amicon YM10). Sodium periodate (0.2 g) dissolved in the sodium acetate buffer (5 ml) was added and kept at +8° C. for one day. Ethylene glycol (0.5 ml) was added and the mixture was left at room temperature for a few hours, then the solution was desalted by ultrafiltration. The periodate oxidized heparin was dissolved in 0.1 M sodium hydroxide and left at room temperature for two hours and then reduced by sodium borohydride (14 mg). Excess sodium borohydride was decomposed by acetic acid (0.2 ml) and the retentate was freeze-dried.

Example 4

Depolymerization of Heparin

Depolymerization of either native or super sulfated heparin was carried out by means of heparanase I (EC 4.2.2.7), in a pH 7 phosphate buffer solution, in the presence of sodium chloride and BSA (bovine serum albumin), at a temperature of between 10-18° C., and preferably 15° C., for 8 to 10 days, and preferably 9 days. The depolymerization was stopped by heating the reaction medium at 100° C. for two minutes, and the mixture was recovered by lyophilization. 7 IU of heparanase I was used per 25 g of heparin. The phosphate buffer solution comprised 0.05 mol/l of $NaH_2PO_4/Na_2HPO_4$ (pH 7) in the presence of 0.1 mol/l of sodium chloride.

Example 5

Inhibition of Tissue Factor-Mediated Hypercoagulable State in Human Whole Blood Using Thrombelastography by Oxidized Ultra-LMWH as Compared to LMWH and Standard Heparin The effects of oxidized ultra-LMWH as compared to LMWH and standard heparin on platelet/fibrin clot dynamics was investigated. A Whole Blood Coagulation Analyzer, Model 5000 Thrombelastograph (TEG®) (Haemoscope Corporation, Skokie, Ill.) was obtained. Recombinant tissue factor (10 mg/vial) was obtained from Dade, Inc. (Miami, Fla.). All other general reagents not specified were obtained from Sigma Co. (Saint Louis, Mo.). The principle of TEG is based on the measurement of the physical viscoelastic characteristics of blood clots (Mousa et al., *Thrombosis Research*, 104 (1):49-56 (2001); Mousa, *Seminar in Thrombosis & Haemostasis*, 26(1) Suppl. 1:39-46 (2000); Mousa et al., *Arteriosclerosis, Thrombosis & Vascular Biology*, 20:1162-1167 (2000), which are hereby incorporated by reference in their entirety). Clot formation was monitored at 37° C. with an oscillating plastic cylindrical cuvette ("cup") and a coaxially suspended stationary piston ("pin") with a 1 mm clearance between the surfaces. The cup oscillates in either direction every 4.5 seconds with a 1 second mid-cycle stationary period resulting in a frequency of 0.1 Hz. The pin is suspended by a torsion wire that acts as a torque transducer. During clot formation, fibrin fibrils physically link the cup to the pin and the rotation of the cup is transmitted to the pin via the viscoelasticity of the clot, which is displayed on-line using an IBM-compatible personal computer and customized software (Haemoscope Corp., Skokie, Ill.).

Figure 2:
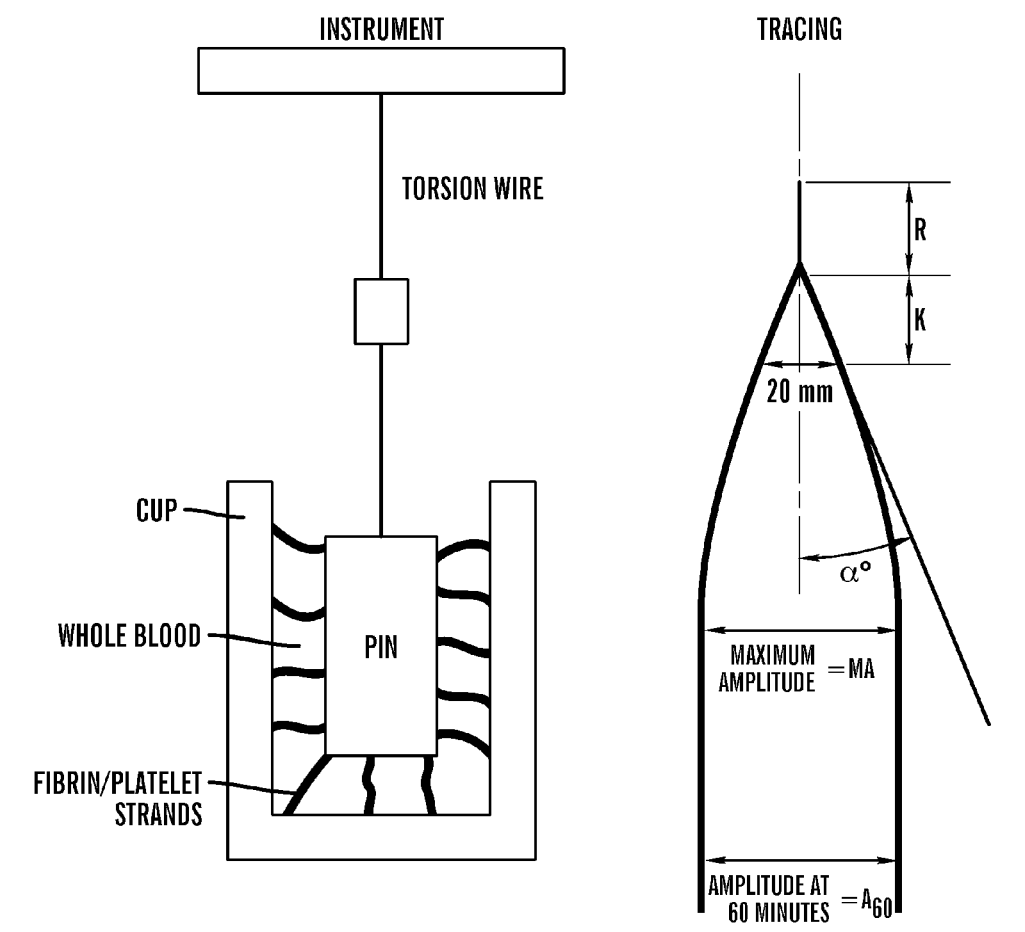
FIG. 2 is an illustration of a thrombelastograph and representative tracing for the assessment of platelet/fibrin clot dynamics.
Figure 3:
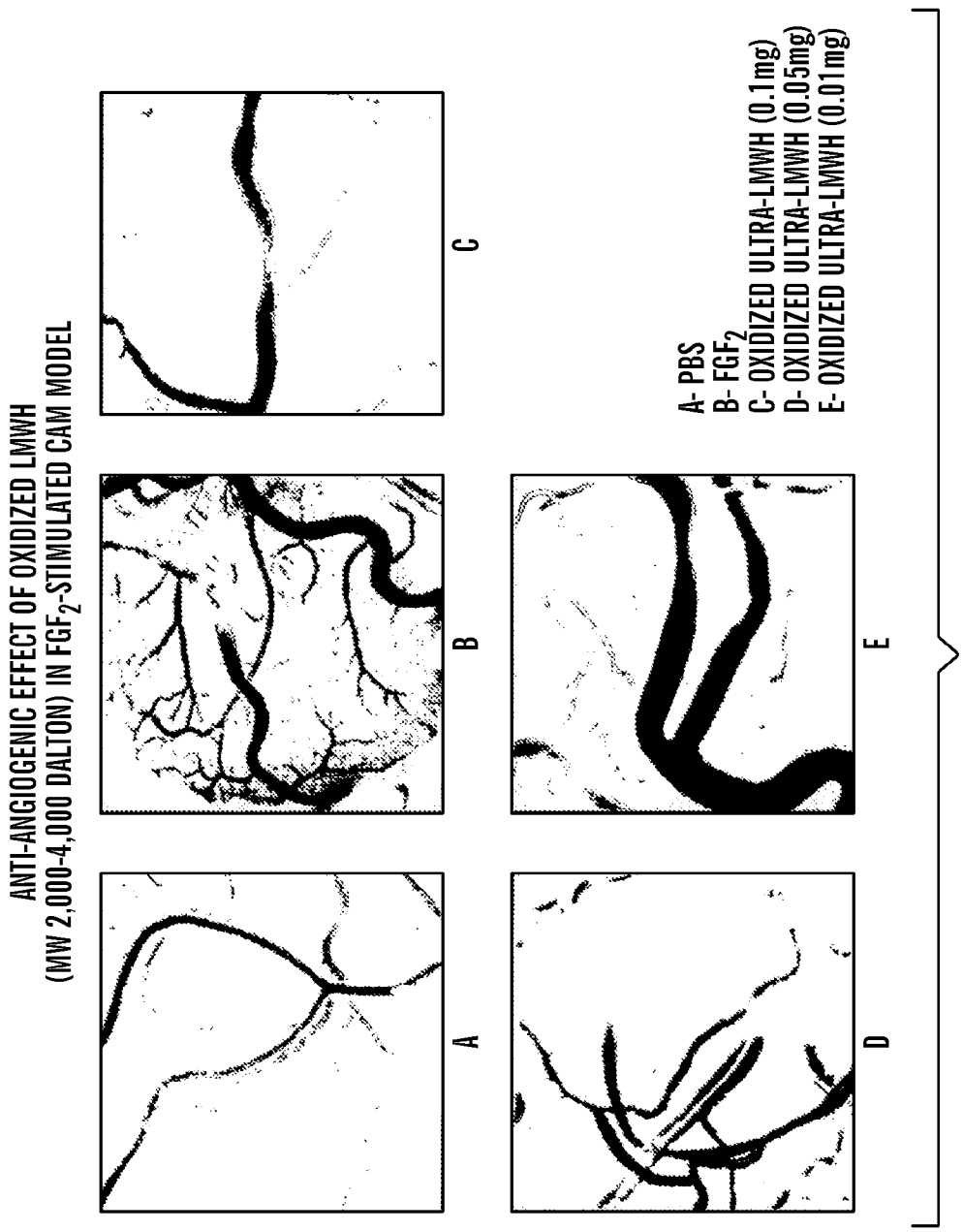
FIGS. 3A-E show the anti-angiogenesis efficacy of oxidized ultra-LMWH at 0.01-1.0 mg in inhibiting FGF2-induced angiogenesis in the chorioallantoic membrane (CAM) model.

Human whole blood was collected into siliconized Vacutainer tubes (Becton Dickinson, Rutherford, N.J.) containing 3.2% trisodium citrate such that a ratio of citrate to whole blood of 1:9 (v/v) was maintained. TEG was performed within three hours of blood collection on a slow speed rocker. Calcium was added back at an average of 2.25 mM concentration followed by the addition of tissue factor (25 ng/cup). Test agent was added with the calcium and tissue factor. Platelet/fibrin clot strength (MA) was monitored (MA (Maximum Amplitude, mm): A direct function of the maximum dynamic properties of fibrin and platelet bonding and represents the ultimate strength of the platelet/fibrin clot. MA is the peak rigidity manifested by the clot at 45-90 minutes) (see FIG. 2). The results are shown in Table 1, below.

The data shown in Table 1 below illustrate the limited anticoagulant effects of oxidized ultra-LMWH or oxidized super sulfated ultra-LMWH as compared to standard heparin (Sigma (Saint Louis, Mo.)) or LMWH.

TABLE 1

Efficacy of oxidized ultra-LMWH in inhibiting tissue factor-mediated hypercoagulable state as compared to other LMWHs in human whole blood using thrombelastography.

| Test agent | Mol. Weight | [Concentration] μg | Mean % Inhibition of Platelet/Clot Strength ± SD |
|---|---|---|---|
| Control | | | 12 ± 0.2 |
| Oxidized super-sulfated ultra-LMWH | 2,000-4,000 daltons | 30.0 | 75 ± 7.5 |
| | | 10.0 | 20 ± 1.5 |
| | | 3.0 | 15 ± 0.8 |
| | | 1.0 | 11 ± 0.1 |
| Oxidized ultra-LMWH | 2,000-4,000 daltons | 30.0 | 54 ± 4.5 |
| | | 10.0 | 15 ± 0.5 |
| | | 3.0 | 12 ± 0.3 |
| | | 1.0 | 11 ± 0.1 |
| Dalteparin ™ (LMWH) | 5,500 daltons (ave. mol. weight) | 1.0 | 96 ± 4 |
| | | 0.3 | 36 ± 2 |
| | | 0.1 | 15 ± 3 |
| Heparin | 12,000 daltons (ave. mol. weight) | 1.0 | 100 ± 5 |
| | | 0.3 | 60 ± 10 |
| | | 0.1 | 32 ± 5 |

Data represent mean ± SD, n = 3.

Example 6

Anticoagulant Effects of Oxidized Ultra-LMWH as Compared to LMWH and Standard Heparin Venous human blood was collected from three volunteers into citrated Vacutainer tubes and centrifuged for 15 minutes at 850 rpm in a Sorvall RT6000 tabletop centrifuge with H-100 B rotor at room temperature. The platelet-rich plasma was removed and the remaining blood was centrifuged for 15 minutes at 26,780 rpm at room temperature to obtain platelet-poor plasma (PPP). A fibrometer was used to measure the clotting time of the activated PPP. Approximately 100 μl of automated activated partial thromboplastin reagent (APTT) was pipetted into a fibrometer cup and incubated at 37° C. for one minute. 100 μl PPP was then added to the cup of heated APTT and allowed to sit for five minutes at 37° C. The preheated cup containing APTT and PPP was then placed under the fibrometer probe prior to activation. Immediately following plasma-activation, the fibrometer timer was set and the clotting determined. Following each trial, the fibrometer probe was cleaned using a Kim wipe dampened in ethanol. The control clotting times of the human plasma from each subject were obtained by activating the plasma with 100 μl of preheated (37° C.) $CaCl_2$ (0.025M). The clotting times of the fibrin inhibitors (heparins) during $Ca^{++}$ activation were determined by adding 12 μl of the heparin derivatives followed immediately by 100 μl of $CaCl_2$. Trials measuring the efficacy of the heparin inhibitor in $Ca^{++}$-activated PPP were conducted by adding 12 μl of the inhibitor during the five minutes of PPP incubation followed by 12 μl of the agonist and 100 μl of $CaCl_2$. A similar procedure was used in testing the PPP, agonists, and inhibitors in tumor cell/tissue factor media. Approximately 20 μl of the tumor media (19.4 mg/ml) and 20

μl of $CaCl_2$ (0.025M) was substituted for the 100 μl of $CaCl_2$ in the calcium-activated trials. The fibrometer was calibrated using lyophilized, buffered human plasma.

The effects of oxidized ultra-LMWH of Example 2 (derivative 1) and the oxidized super sulfated ultra-LMWH of Example 3 as compared to LMWH (Dalteparin™) on various coagulation parameters including prothrombin time (PT) and APTT were determined in human plasma. Oxidized ultra-LMWH of Example 2 and the oxidized super sulfated ultra-LMWH of Example 3 demonstrated a much weaker anti-coagulant effect as compared to other LMWH (Dalteparin™). This was achieved while maintaining strong anti-angiogenesis potency as shown in Table 2 below.

TABLE 2

Effect of oxidized ultra-LMWH on different coagulation parameters.

| Test agent | Average Molecular Weight | Conc. (μg) | PT ± SD (Seconds) | APTT ± SD (Seconds) |
|---|---|---|---|---|
| Control | | | 12 ± 0.2 | 26 ± 2.0 |
| Oxidized super sulfated ultra-LMWH | 2,000-4,000 daltons | 10.0 | 14 ± 0.5 | 40 ± 5 |
| | | 3.0 | 12 ± 0.2 | 28 ± 2 |
| | | 1.0 | 11 ± 0.1 | 26 ± 1 |
| Oxidized LMWH | 2,000-4,000 daltons | 10.0 | 16 ± 0.5 | 52 ± 5 |
| | | 3.0 | 12 ± 0.3 | 38 ± 2 |
| | | 1.0 | 11 ± 0.1 | 27 ± 1 |
| Dalteparin ™ (LMWH) | 5,500 daltons (ave. mol. weight) | 1.0 | 26 ± 0.5 | ≻400 |
| | | 0.3 | 16 ± 0.2 | 200 ± 10 |
| | | 0.1 | 12 ± 0.1 | 40 ± 3 |
| Standard Heparin (Sigma (Saint Louis, MO)) | 12,000 daltons (ave. mol. weight) | 1.0 | 160 ± 5 | ≻400 |
| | | 0.3 | 30 ± 1 | ≻400 |
| | | 0.1 | 12 ± 0.2 | 55 ± 5 |

Data represent mean time in Seconds ± SD, n = 3.

Example 7

Inhibition of Endothelial Cell Tube Formation

Differentiation by endothelial cells was examined using a method developed by Grant et al. (Grant et al., *In Vitro Cell Dev. Biol.*, 27A:327-336 (1991), which is hereby incorporated by reference in its entirety). Matrigel® matrix, phenol-red free (commercially available from Becton Dickinson, Bedford, Mass.) was thawed overnight at 4° C. Using cold pipette tips, 3.0 mg/well of Matrigel® matrix was placed in a cold twenty-four-multiwell plate (Falcon). Matrigel® matrix was allowed to polymerize during incubation at 37° C. for 30 minutes.

Human umbilical vein endothelial cells (HUVEC) were maintained at 37° C. with 5% $CO_2$ and 95% humidity in endothelial cell growth medium with 2% fetal bovine serum (EGM). The tube assay was performed in endothelial cell basal medium (EBM) supplemented with 0.5% bovine serum albumin (BSA) and 1:100 diluted Insulin-Transferrin-Selenium-G supplement (I-T-Se, 100×). HUVEC were trypsinized and centrifuged and, subsequently, washed twice in phosphate buffered saline (PBS). After counting, cell density was adjusted to 35,000 cells/mL.

A final concentration of 35,000 cells/mL/well was treated with recombinant human fibroblast growth factor basic (FGF2) at 100 ng/ml and oxidized LMWH of Examples 2 (derivative 1) and 3 (see Table 3 below) dissolved in EBM medium to a concentration of 0.015 μmol. Treated cells were incubated overnight at 37° C. with 5% $CO_2$ and 95% humidity to allow cell attachment.

Subsequently, the medium was aspirated and cells were fixed and stained using a modified HEMA-3 stain kit. Digital images of micro-titer well sections were collected using a DKC5000 3-CCD color video camera system (Toshiba America, New York, N.Y.) and analyzed using Image-Pro Plus software (Media Cybernetics, Silver Spring, Md.). The area and major axis length of stained cells having a tubular morphology was measured on the Matrigel® matrix surface (Becton Dickinson, Bedford, Pa.) counted from 5 images/well.

Table 3 below clearly illustrates that oxidized ultra-LMWH and oxidized super sulfated ultra-LMWH are very potent inhibitors of FGF2-stimulated EC tube formation in vitro.

TABLE 3

Microscopic Analysis of EC Tube Formation

| Treatment | Concentration | Cell Tube Formation (area, $mm^2$) | Cell Tube Formation (length, mm) |
|---|---|---|---|
| PBS | — | 1.05 ± 0.11 | 41.36 ± 2.61 |
| FGF2 | 100 ng/ml | 2.50 ± 0.28 | 79.83 ± 8.66 |
| FGF2 + Oxidized Ultra-LMWH* | 100 ng/ml + 1 μg | 1.10 ± 0.12 | 47.54 ± 4.31 |
| FGF2 + oxidized S-S Ultra-LMWH* | 100 ng/ml + 1 μg | 1.00 ± 0.10 | 40.20 ± 2.35 |
| Dalteparin ™ (LMWH) | 100 ng/ml + 10 μg | 1.20 + 0.12 | 45.50 + 3.40 |

*Oxidized Ultra-LMWH or oxidized super-sulfated (S-S) ultra-LMWH were added at 100 μl (Final Concentration 1 μg).

Example 8

Neovascularization on the Chick Chorioallantoic Membrane (CAM) and Microscopic Analysis of CAM Sections In vivo neovascularization was examined by the method previously described by Auerbach et al. (Auerbach et al., *J. Dev. Biol.*, 41:391-394 (1974), which is hereby incorporated by reference in its entirety). Ten-day old embryos were purchased from Spafas, Inc. (Preston, Conn.) and were incubated at 37° C. with 55% relative humidity. In the dark with the help of a candling lamp, a small hole was punctured in the shell concealing the air sac with a hypodermic needle. A second hole was punctured in the shell on the broadside of the egg directly over an avascular portion of the embryonic membrane, as observed during candling. A false air sac was created beneath the second hole by the application of negative pressure to the first hole, which caused the chorioallantoic membrane (CAM) to separate from the shell. A window, approximately 1.0 $cm^2$, was cut in the shell over the dropped CAM with the use of a small crafts grinding wheel (Dremel, Division of Emerson Electric Company Racine, Wis.) which allowed direct access to the underlying CAM. Filter disks of #1 filter paper (Whatman International, United Kingdom) were soaked in 3 mg/mL cortisone acetate (Sigma, St. Louis, Mo.) in a solution of 95% ethanol and water and subsequently air dried under sterile conditions. FGF2 (Life Technologies, Gaithersburg, Md.) was used to grow vessels on the CAMs of 10 day old chick embryos. Sterile filter disks adsorbed with FGF2 dissolved in PBS at 1 μg/mL were placed on growing CAMs. At 24 hours, test compound (oxidized ultra-LMWH of Example 2 (derivative 1), oxidized super sulfated ultra-LMWH of Example 3, or Dalteparin™) or control vehicle was added directly to CAMs topically.

CAM tissue directly beneath FGF2-saturated filter disk was resected from embryos treated 48 hours prior with test compound or control. Tissues were washed three times with PBS. Sections were placed in a 35-mm petri dish (Nalge Nunc, Rochester, N.Y.) and examined under a SV6 stereomicroscope (Karl Zeiss, Thornwood, N.Y.) at 50× magnification. Digital images of CAM sections adjacent to filters were collected using a 3-CCD color video camera system (Toshiba America, New York, N.Y.) and analyzed using Image-Pro Plus software (Media Cybernetics, Silver Spring, Md.). Table 4 contains the number of vessel branch points contained in a circular region equal to the area of a filter disk counted for each section.

TABLE 4

Anti-angiogenic effect of oxidized ultra-LMWH in the CAM Model.

| Sample | Average # of Branch Points |
| --- | --- |
| PBS control | 95 ± 11 |
| FGF2 | 264 + 18 |
| FGF2 + Dalteparin ™ (LMWH) 10 µg | 155 ± 14 |
| FGF-2 + 10 µg Oxidized Ultra-LMWH | 94 ± 08 |
| FGF-2 + 10 µg Oxidized S-S Ultra-LMWH | 90 ± 10 |

The anti-angiogenesis efficacy of oxidized ultra-LMWH of Example 2 at 0.01-1.0 mg in inhibiting FGF2-induced angiogenesis in the CAM model was then tested. The results are shown in FIGS. 3A-E.

Results from the above assays showed that 10 µg of oxidized ultra-LMWH and oxidized super sulfated (S-S) ultra-LMWH were effective in controlling FGF2-stimulated new blood vessel formation in the CAM (100% inhibition at 10 µg).

Figure 4A:
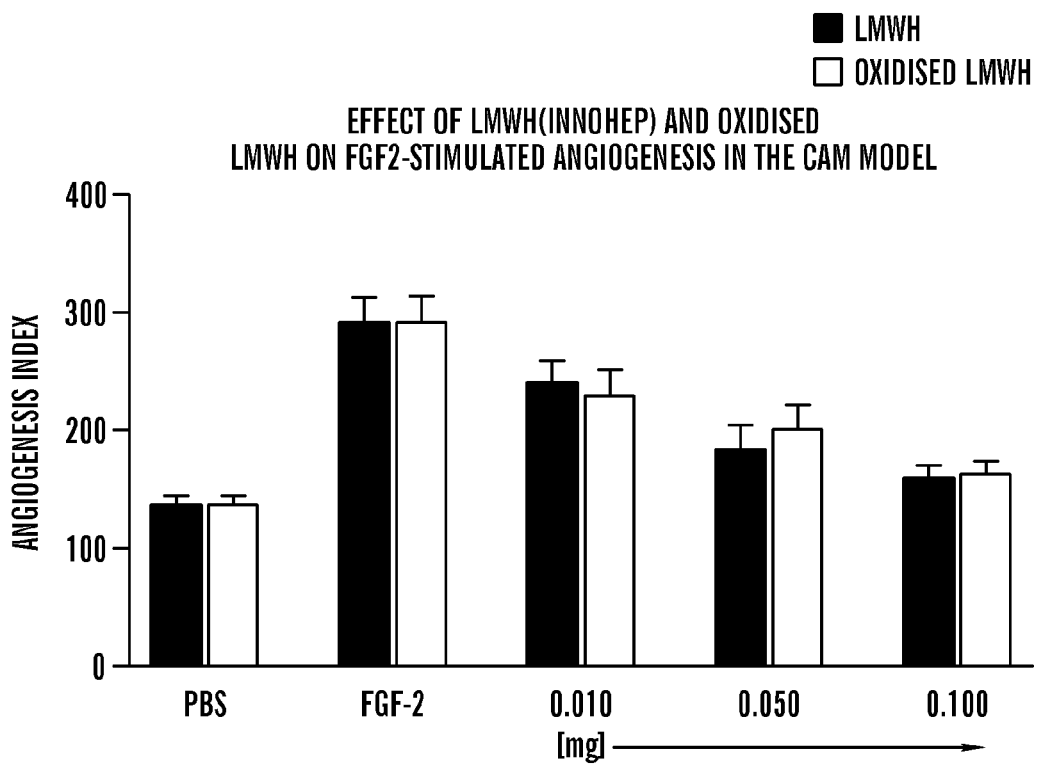
FIGS. 4A-B are graphs showing comparative anti-angiogenesis efficacy between Innohep™ (Tinzaparin™), a LMWH with a relatively high molecular weight distribution (average molecular weight=6,500 daltons and high percentage of 6,000-8,000 daltons) and potent anticoagulant efficacy, and an oxidized ultra-LMWH fraction (molecular weight=2,000-4,000 daltons) of the present invention.
Figure 4B:
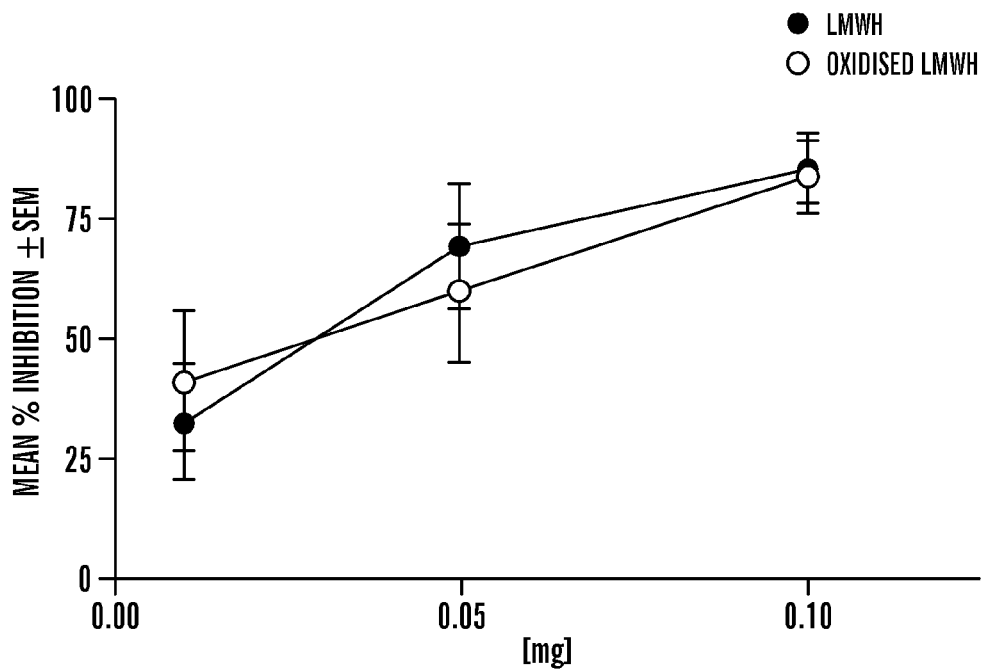

The anti-angiogenesis activity of the oxidized ultra-LMWH of the present invention (of Example 2—derivative 1) and Innohep™ (Tinzaparin™), a LMWH with a relatively high molecular weight distribution (average molecular weight of 6,500 daltons, with a high percentage of 6,000-8,000 daltons) and a potent anticoagulant as compared to other LMWH (Mousa, *Seminar in Thrombosis & Haemostasis*, 26(1) Suppl. 1:39-46 (2000), which is hereby incorporated by reference in its entirety), was then compared. The results are shown in FIGS. 4A-B.

Example 9

Chick Chorioallantoic Membrane (CAM) Tumor Assays

Ten million tumor cells were placed on the surface of each CAM and were cultured for one week. The resulting tumors were excised and cut into 50 mg fragments. These fragments were placed on additional CAMs and treated topically or systemically by intravenous injection the following day with the test agents. Forty-eight hours later, CAMs were excised from the egg and the numbers of blood vessels entering the tumors were counted (as vessel branch points). Each treatment group incorporated at least ten tumors per experiment. Tumors were then excised from the egg and tumor weights were determined for each tumor. Oxidized ultra-LMWH (Example 2—derivative 1) as compared to r-tissue factor pathway inhibitor (r-TFPI) was effective in blocking tumor growth, including colon and fibrosarcoma tumor growth, as shown in Table 5 below.

TABLE 5

Effect of oxidized ultra-LMWH or r-TFPI on tumor growth in the CAM tumor implant model

| | Mean tumor weight (mg) ± SEM | | |
| --- | --- | --- | --- |
| Tumor Type | Control | Oxidized Ultra-LMWH | r-TFPI |
| Colon | 83 ± 8 | 22 ± 5* | 38 ± 8* |
| Fibrosarcoma | 325 ± 32 | 85 ± 15* | 120 ± 25* |

Data represent mean + SEM, n = 8 per group. Initial tumor implant averaged 45 ± 5 mg. Oxidized ultra-LMWH or r-TFPI was dosed at 0.10 mg or 0.01 mg, respectively as a single dose over 7 days.
*P < 0.01

Example 10

Effect of Oxidized Ultra-LMWH on Endothelial Tissue Factor Pathway Inhibitor (TFPI) Release The effect of heparin molecular weight fractions and different LMWH derivatives on the release of TFPI from human umbilical vein endothelial cells (HUVEC) was determined over a 24 hour incubation.

HUVEC media samples were incubated in micro-test wells pre-coated with a rabbit anti-human TFPI polyclinic antibody. TFPI was detected using a biotinylated monoclonal antibody specific for kunitz domain 1 TFPI (Hoppensteadt et al., *Thromb Res.* 77(2):175-185 (1995), which is hereby incorporated by reference in its entirety). The subsequent binding of the streptavidin conjugated horseradish peroxidase (HRP) completes the formation of the antibody enzyme detection complex. The addition of TMB substrate and its subsequent reaction with HRP provides a blue color that converts to yellow color upon the addition of sulfuric acid. TFPI levels were determined by measuring sample solution absorbance at 450 nM and comparing against a standard calibration curve using native TFPI. Oxidized ultra-LMWH and oxidized super sulfated ultra-LMWH were effective inducers of TFPI release from human endothelial cells, as shown in Table 6 below.

TABLE 6

Effect of oxidized ultra-LMWH on endothelial TFPI release.

| Test agent | Average Molecular Weight | Conc. (µg) | Mean TFPI ± SD (ng/$10^6$ EC) |
| --- | --- | --- | --- |
| Control | | | 1.8 ± 0.2 |
| Oxidized S-S Ultra-LMWH | 2,000-4,000 daltons | 1.0 | 18 ± 1.0 |
| | | 0.3 | 6.5 ± 0.4 |
| | | 0.1 | 3.3 ± 0.2 |
| Oxidized Ultra-LMWH | 2,000-4,000 daltons | 1.0 | 12 ± 1.3 |
| | | 0.3 | 5.2 ± 0.4 |
| | | 0.1 | 3.1 ± 0.2 |
| Tinzaparin ™ (Innohep ™) (LMWH) | 6,500 daltons | 1.0 | 7.8 ± 0.5 |
| | | 0.3 | 4.6 ± 0.2 |
| | | 0.1 | 3.2 ± 0.1 |
| Enoxaparin ™ (Lovenax ™) (LMWH) | 4,500 daltons | 1.0 | 4.5 ± 0.6 |
| | | 0.3 | 3.0 ± 0.3 |
| | | 0.1 | 2.2 ± 0.2 |

Data represent mean TFPI release over 6 hours ± SD, n = 3.

Figure 5:
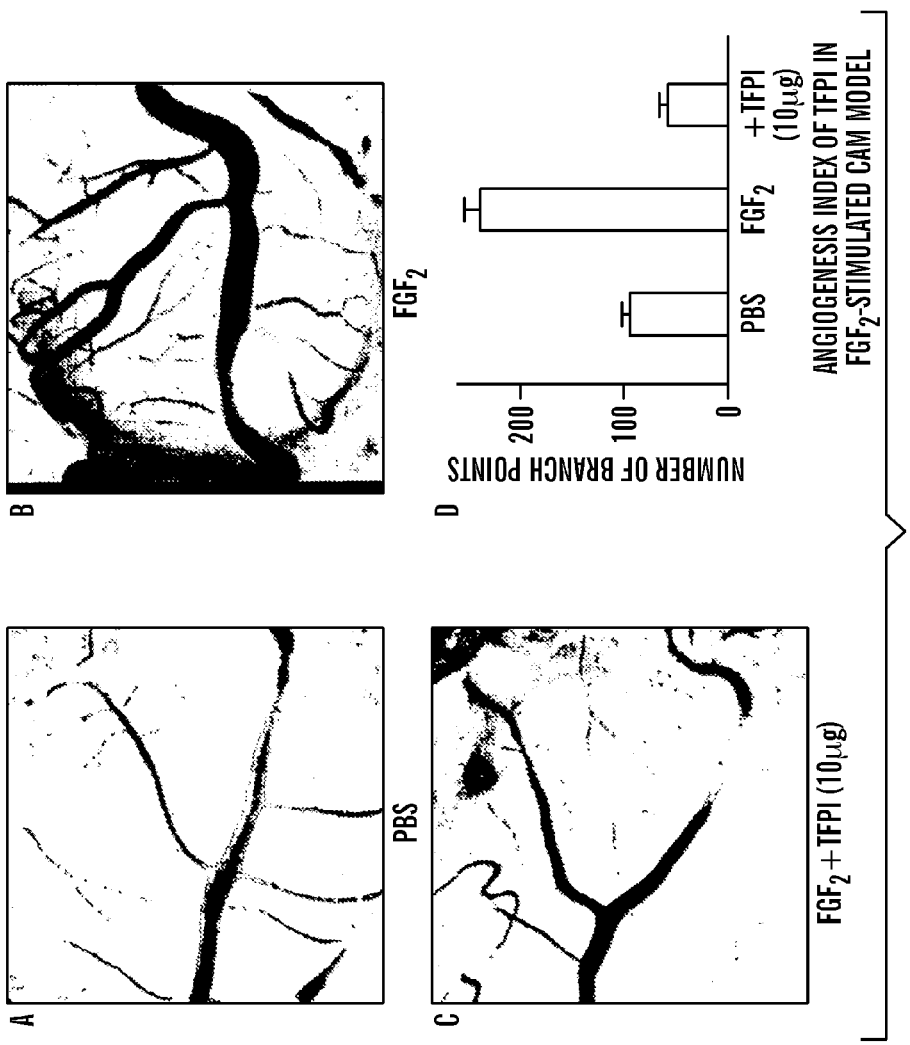
FIGS. 5A-D show the anti-angiogenesis efficacy of tissue factor pathway inhibitor (TFPI) in inhibiting FGF2-induced angiogenesis in the CAM model.

Data demonstrated equal to greater potency for oxidized super sulfated (S-S) ultra-LMWH or oxidized ultra-LMWH in releasing endothelial TFPI (Table 6). FIG. 5 shows the anti-angiogenic effect of TFPI in the FGF2 induced CAM model. Thus, the greater potency of oxidized super sulfated ultra-LMWH or oxidized LMWH of the present invention results in a greater anti-angiogenic effect for these fractions also.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An oxidized heparin fraction having a molecular weight of from about 2,000 to about 4,000 daltons,
   wherein the oxidized heparin fraction is super-sulfated such that the super-sulfated oxidized heparin fraction comprises an anticoagulant reduction characteristic and an angiogenesis inhibition characteristic;
   wherein the super-sulfated oxidized heparin fraction has a chemical structure of a first oxidized heparin fraction after the first oxidized heparin fraction has been O-sulfated by sulfate substitution at oxygen bonds within repeating units of the first oxidized heparin fraction; and
   wherein the percentage of hydroxyl residues of the heparin fraction are oxidized is in a range of 25 percent to 100 percent.

2. The oxidized heparin fraction of claim 1, wherein the percentage of hydroxyl residues of the constituents that are oxidized is in a range of 50 percent to 100 percent.

3. The oxidized heparin fraction of claim 1, wherein the percentage of hydroxyl residues in the oxidized heparin fraction that are oxidized is in a range of 90 percent to 100 percent.

4. The oxidized heparin fraction of claim 1, wherein the super-sulfated oxidized heparin fraction fully inhibits fibroblast growth factor (FGF2) induced angiogenesis.

5. The oxidized heparin fraction of claim 1, wherein the super-sulfated oxidized heparin fraction comprises a sulfate to carboxylate ratio of about 5:1.

6. The oxidized heparin fraction of claim 1, wherein from about 50% to about 100% of primary hydroxyls in glucosamine residues and secondary hydroxyl groups in disaccharide units are substituted by O-sulfate esters in the O-sulfated oxidized heparin fraction.

7. The oxidized heparin fraction of claim 1,
   wherein the anticoagulant reduction characteristic comprises a first anticoagulant reduction characteristic, a second anticoagulant reduction characteristic, or a combination thereof;
   wherein the first anticoagulant reduction characteristic is that the oxidized heparin fraction reduces a mean percent inhibition of platelet clot strength by factor of at least about 8 relative to a mean percent inhibition of platelet clot strength of unfractionated heparin under a condition of the concentration of the oxidized heparin fraction in human blood being equal to the concentration of the unfractionated heparin in human blood;
   wherein the second anticoagulant reduction characteristic is that the oxidized heparin fraction reduces a prolongation of clotting time of human blood by at least 75% relative to a prolongation of clotting time of human blood by unfractionated heparin under a condition of the concentration of the oxidized heparin fraction in human blood being equal to the concentration of the unfractionated heparin in human blood, subject to the clotting time being a prothrombin time (PT) or an activated partial thromboplastin time (APTT); and
   wherein the angiogenesis inhibition characteristic is that the oxidized heparin fraction in an endothelial cell (EC) growth medium cancels an effect of recombinant human fibroblast growth factor (FGF2) on EC tube formation in the EC growth medium under a condition of the concentration of FGF2 in the EC growth medium being sufficient to increase a length or area of the EC tube formation by a factor of at least about 2 if the oxidized heparin fraction is not in the EC growth medium.

8. The oxidized heparin fraction of claim 7, wherein the anticoagulant reduction characteristic comprises the first anticoagulant reduction characteristic.

9. The oxidized heparin fraction of claim 7, wherein the anticoagulant reduction characteristic comprises the second anticoagulant reduction characteristic.

10. A composition comprising from about 60% to about 100% of the oxidized heparin fraction of claim 1, and from about 0% to about 40% of heparin, low molecular weight heparin, chondroitin sulfates, dermatan sulfates, heparan sulfates, heparin derivatives, or combinations thereof.

11. The composition of claim 10, further comprising a non-heparin anticoagulant selected from the group consisting of anti-Xa compounds, anti-IIa compounds, anti-tissue factor compounds, anti-VIIa compounds, and combinations thereof.

12. The composition of claim 10, further comprising a non-heparin angiogenic inhibitor selected from the group consisting of integrin inhibitory compounds, angiostatin, endostatin, fibroblast growth factor inhibitors, fibroblast growth factor receptor inhibitors, vascular endothelial growth factor inhibitors, thrombospondin, platelet factor 4, interferon, interleukin 12, thalidomide, and combinations thereof.

13. The composition of claim 10, further comprising a cytotoxic or chemotherapeutic agent selected from the group consisting of nitrogen mustard, aziridine thiotepa, alkyl sulfonate, nitrosoureas, platinum complexes, non-classic alkylators, substituted urea, antitumor antibiotics, microtubule agents, and asparaginase.

14. A polymeric structure comprising the oxidized heparin fraction of claim 1, wherein said oxidized heparin fraction is covalently attached to the polymeric structure by surface grafting or copolymerization, non-covalently incorporated into a matrix of the polymeric structure, or encapsulated as a biomedical material within the polymeric structure.

15. The polymeric structure of claim 14, wherein said oxidized heparin fraction is non-covalently incorporated into the matrix.

16. The polymeric structure of claim 15, wherein the matrix comprises a biocompatible polymer and provides for a sustained release of said oxidized heparin fraction.

17. The polymeric structure of claim 14, wherein said oxidized heparin fraction is covalently attached to the polymeric structure by surface grafting or copolymerization.

18. The polymeric structure of claim 14, wherein said oxidized heparin fraction is encapsulated as said biomedical material within the polymeric structure.

19. A method, comprising forming the oxidized heparin fraction of claim 1, wherein said forming the oxidized heparin fraction comprises O-sulfating the first oxidized heparin fraction by performing sulfate substitution at oxygen bonds within repeating units of the first oxidized heparin fraction.

* * * * *